(12) United States Patent
Yoneda et al.

(10) Patent No.: US 11,072,580 B2
(45) Date of Patent: Jul. 27, 2021

(54) SULFURIC ACID ESTER OR SALT THEREOF, AND SURFACTANT

(71) Applicant: DAIKIN INDUSTRIES, LTD., Osaka (JP)

(72) Inventors: Satoru Yoneda, Osaka (JP); Manabu Fujisawa, Osaka (JP); Kazuya Asano, Osaka (JP); Takahiro Kitahara, Osaka (JP); Masahiro Higashi, Osaka (JP); Akiyoshi Yamauchi, Osaka (JP); Sumi Ishihara, Osaka (JP); Yosuke Kishikawa, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 201 days.

(21) Appl. No.: 16/338,250

(22) PCT Filed: Sep. 29, 2017

(86) PCT No.: PCT/JP2017/035370
§ 371 (c)(1),
(2) Date: Mar. 29, 2019

(87) PCT Pub. No.: WO2018/062448
PCT Pub. Date: Apr. 5, 2018

(65) Prior Publication Data
US 2020/0172476 A1 Jun. 4, 2020

(30) Foreign Application Priority Data
Sep. 30, 2016 (JP) .............................. JP2016-195060

(51) Int. Cl.
*C07C 305/04* (2006.01)

(52) U.S. Cl.
CPC .................................. *C07C 305/04* (2013.01)

(58) Field of Classification Search
None
See application file for complete search history.

(56) References Cited

U.S. PATENT DOCUMENTS

| | | |
|---|---|---|
| 2007/0032550 A1 | 2/2007 | Lewis et al. |
| 2009/0181952 A1 | 7/2009 | Haydar et al. |
| 2012/0172580 A1 | 7/2012 | Masuta et al. |
| 2015/0164072 A1 | 6/2015 | Kageyama et al. |

FOREIGN PATENT DOCUMENTS

| | | |
|---|---|---|
| JP | 49-133677 A | 12/1974 |
| JP | 8-81357 A | 3/1996 |
| JP | 8-301747 A | 11/1996 |
| JP | 10-338617 A | 12/1998 |
| JP | 2001-172669 A | 6/2001 |
| JP | 2014-37406 A | 2/2014 |
| WO | 2011/030816 A1 | 3/2011 |

OTHER PUBLICATIONS

H. Schlenk, et al.: "Syntheses of derivatives of dihydroxyacetone and of glycerides", Journal of the American Chemical Society, vol. 74, No. 10, May 1, 1952, pp. 2550-2552 ( 3 pages total).
Robert Irwin et al., "Steroid Potentiation and Inhibition of N-Methyl-D-Aspartate Receptor-Mediated Intracellular Ca++Responses: Structure Activity Studies", The Journal of Pharmacology and Experimental Therapeutics, vol. 271 No. 2, 1994, pp. 677-682 ( 6 pages total).
J.M Basford et al., "A Possible Route to the Production of Free L-Tyrosine O-Sulphate by the Rat", Biochem J., vol. 99, No. 534, 1966, pp. 534-537 (4 pages total).
Deepak B. Salunke et al., "Design and Development of Stable, Water-Soluble Human Toll-like Receptor 2 Specific Monoacyl Lipopeptides as Candidate Vaccine Adjuvants", Journal of Medicinal Chemistry, vol. 56, 2013, pp. 5885-5900 (16 pages total).
Andrew M. King et al. "Structural and Kinetic Characterization of Diazabicyclooctanes as Dual Inhibitors of Both Serine-β-Lactamases and Penicillin-Binding Proteins", American Chemical Society Chemical Biology, vol. 11, No. 4, 2016, pp. 864-868 (5 pages total).
Communication dated May 26, 2020, from the European Patent Office in application No. 17856397.9.
Aoyama et al., "Stereoselective Total Synthesis of (−)-α-Eudesmol, a P/Q-type Calcium Channel Blocker", Synlett, No. 9, pp. 1452-1454, 2001, 3 pages total.
Reddy et al., "Synthesis and Evaluation of Surface and Biological Properties of Some Lactic Acid-Based Anionic Surfactants", J. Surfact. Deterg., vol. 19, pp. 343-351, 2016, 9 pages total.
Xin Fan et al., "Oxygenated Hydrocarbon Ionic Surfactants Exhibit CO2 Solubility", J. Am. Chem. Soc. , 2005, pp. 11754-11762, vol. 127.
Gregory R. Schulz et al., "Micelles formed from photochemically active amphiphiles: structural characterization by small-angle neutron scattering", Journal of Molecular Structure, 1996, pp. 191-196, vol. 383.
International Search Report for PCT/JP2017/035370, dated Oct. 31, 2017.
International Preliminary Report on Patentability with translation of written opinion dated Apr. 2, 2019, in counterpart International Application No. PCT/JP2017/035370.

(Continued)

*Primary Examiner* — Joseph R Kosack
(74) *Attorney, Agent, or Firm* — Sughrue Mion, PLLC

(57) ABSTRACT

A sulfuric acid ester containing a plurality of carbonyl groups or a salt thereof, and a surfactant. The sulfuric acid ester is a compound represented by the following formula:

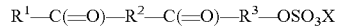

$R^1-C(=O)-R^2-C(=O)-R^3-OSO_3X$ wherein $R^1$, $R^2$ and $R^3$ are as defined herein; X is H, a metal atom, $NR^4_4$, imidazolium optionally containing a substituent, pyridinium optionally containing a substituent, or phosphonium optionally containing a substituent, where $R^4$s are each H or an organic group and are the same as or different from each other; and any two of $R^1$, $R^2$, and $R^3$ optionally bind to each other to form a ring.

7 Claims, No Drawings

SULFURIC ACID ESTER OR SALT THEREOF, AND SURFACTANT

CROSS REFERENCE TO RELATED APPLICATIONS

This Application is a National Stage of International Application No. PCT/JP2017/035370 filed Sep. 29, 2017, claiming priority based on Japanese Patent Application No. 2016-195060 filed Sep. 30, 2016.

TECHNICAL FIELD

The invention relates to sulfuric acid esters or salts thereof, and surfactants.

BACKGROUND ART

Non-Patent Literature 1 discloses the following compounds.

[Chem. 1]

1

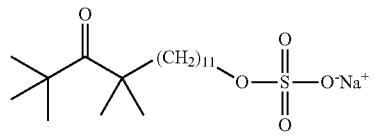

2

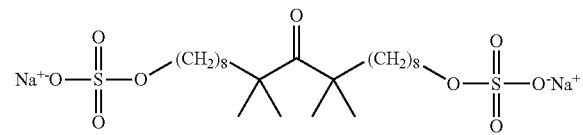

3

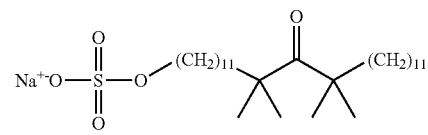

4

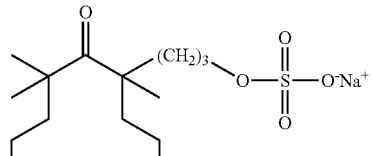

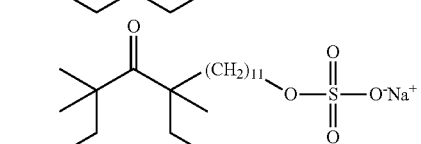

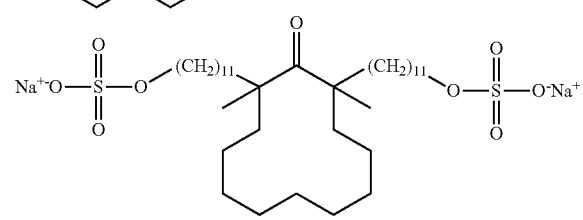

CITATION LIST

Non-Patent Literature

Non-Patent Literature 1: Gregory R. Schulz and 3 other persons, "Micelles formed from photochemically active amphiphiles: structural characterization by small-angle neutron scattering", Journal of Molecular Structure, 383(1-3), 1996, pp. 191-196

SUMMARY OF INVENTION

Technical Problem

The invention aims to provide a novel sulfuric acid ester containing a plurality of carbonyl groups or a salt thereof, and a surfactant.

Solution to Problem

The invention relates to a compound represented by the following formula:

[Chem. 2]

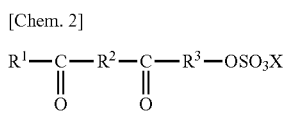

wherein $R^1$ is a linear or branched alkyl group containing one or more carbon atoms or a cyclic alkyl group containing three or more carbon atoms, with a hydrogen atom that binds to a carbon atom being optionally replaced by a hydroxy group or a monovalent organic group containing an ester bond, the alkyl group optionally containing a carbonyl group when containing two or more carbon atoms, and the alkyl group optionally containing a monovalent or divalent heterocycle or being optionally in a cyclized form when containing three or more carbon atoms;

$R^2$ and $R^3$ are each individually a single bond or a divalent linking group;

$R^1$, $R^2$, and $R^3$ contain six or more carbon atoms in total;

X is H, a metal atom, $NR^4_4$, imidazolium optionally containing a substituent, pyridinium optionally containing a substituent, or phosphonium optionally containing a substituent, where $R^4$s are each H or an organic group and are the same as or different from each other; and any two of $R^1$, $R^2$, and $R^3$ optionally bind to each other to form a ring.

In the formula, preferably, $R^2$ and $R^3$ are each individually a single bond, a linear or branched alkylene group containing one or more carbon atoms, or a cyclic alkylene group containing three or more carbon atoms, with a hydrogen atom that binds to a carbon atom being optionally replaced by a hydroxy group or a monovalent organic group containing an ester bond.

In the formula, $R^1$ is preferably a C1-C8 linear or branched alkyl group containing no carbonyl group, a C3-C8 cyclic alkyl group containing no carbonyl group, a C2-C45 linear or branched alkyl group containing 1 to 10 carbonyl groups, a C3-C45 cyclic alkyl group containing a carbonyl group, or a C3-C45 alkyl group containing a monovalent or divalent heterocycle.

In the formula, $R^1$ is preferably a group represented by the following formula:

[Chem. 2]

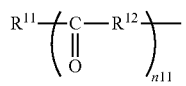

wherein n11 is an integer of 0 to 10; $R^{11}$ is a C1-C5 linear or branched alkyl group or a C3-C5 cyclic alkyl group; and $R^{12}$ is a C0-C3 alkylene group, and when n11 is an integer of 2 to 10, $R^{12}$s are the same as or different from each other.

In the formula, preferably, $R^2$ and $R^3$ are each individually a linear or branched alkylene group containing no carbonyl group and containing one or more carbon atoms.

In the formula, preferably, $R^2$ and $R^3$ are each individually a C1-C3 linear or branched alkylene group containing no carbonyl group.

The invention also relates to a surfactant containing the above compound.

The invention also relates to an aqueous dispersant containing the above compound.

Advantageous Effects of Invention

The compound of the invention is a compound exhibiting a surfactant effect, and can suitably be used for anionic surfactants and aqueous dispersants.

DESCRIPTION OF EMBODIMENTS

The invention will be specifically described hereinbelow.

The term "organic group" as used herein means a group containing one or more carbon atoms or a group obtainable by removing one hydrogen atom from an organic compound, unless otherwise mentioned.

Examples of the "organic group" include:
an alkyl group optionally containing one or more substituents,
an alkenyl group optionally containing one or more substituents,
an alkynyl group optionally containing one or more substituents,
a cycloalkyl group optionally containing one or more substituents,
a cycloalkenyl group optionally containing one or more substituents,
a cycloalkadienyl group optionally containing one or more substituents,
an aryl group optionally containing one or more substituents,
an aralkyl group optionally containing one or more substituents,
a non-aromatic heterocyclic group optionally containing one or more substituents,
a heteroaryl group optionally containing one or more substituents,
a cyano group,
a formyl group,
RaO—,
RaCO—,
RaSO$_2$—,
RaCOO—,
RaNRaCO—,
RaCONRa—,
RaSO$_2$NRa—,
RaNRaSO$_2$—,
RaOCO—, and
RaOSO$_2$—,
wherein each Ra is independently
an alkyl group optionally containing one or more substituents,
an alkenyl group optionally containing one or more substituents,
an alkynyl group optionally containing one or more substituents,
a cycloalkyl group optionally containing one or more substituents,
a cycloalkenyl group optionally containing one or more substituents,
a cycloalkadienyl group optionally containing one or more substituents,
an aryl group optionally containing one or more substituents,
an aralkyl group optionally containing one or more substituents,
a non-aromatic heterocyclic group optionally containing one or more substituents, or
a heteroaryl group optionally containing one or more substituents.

The organic group is preferably an alkyl group optionally containing one or more substituents.

The term "substituent" as used herein means a group which can replace another atom or a group, unless otherwise mentioned. Examples of the "substituent" include an aliphatic group, an aromatic group, a heterocyclic group, an acyl group, an acyloxy group, an acylamino group, an aliphatic oxy group, an aromatic oxy group, a heterocyclic oxy group, an aliphatic oxycarbonyl group, an aromatic oxycarbonyl group, a heterocyclic oxycarbonyl group, a carbamoyl group, an aliphatic sulfonyl group, an aromatic sulfonyl group, a heterocyclic sulfonyl group, an aliphatic sulfonyloxy group, an aromatic sulfonyloxy group, a heterocyclic sulfonyloxy group, a sulfamoyl group, an aliphatic sulfonamide group, an aromatic sulfonamide group, a heterocyclic sulfonamide group, an amino group, an aliphatic amino group, an aromatic amino group, a heterocyclic amino group, an aliphatic oxycarbonylamino group, an aromatic oxycarbonylamino group, a heterocyclic oxycarbonylamino group, an aliphatic sulfinyl group, an aromatic sulfinyl group, an aliphatic thio group, an aromatic thio group, a hydroxy group, a cyano group, a sulfo group, a carboxy group, an aliphatic oxyamino group, an aromatic oxyamino group, a carbamoylamino group, a sulfamoyl amino group, a halogen atom, a sulfamoyl carbamoyl group, a carbamoyl sulfamoyl group, a dialiphatic oxyphosphinyl group, and a diaromatic oxyphosphinyl group.

The aliphatic group may be either saturated or unsaturated, and may contain any of a hydroxy group, an aliphatic oxy group, a carbamoyl group, an aliphatic oxycarbonyl group, an aliphatic thio group, an amino group, an aliphatic amino group, an acylamino group, a carbamoylamino group, and the like. Examples of the aliphatic group include alkyl groups containing one to eight, preferably one to four carbon atoms in total, such as a methyl group, an ethyl group, a vinyl group, a cyclohexyl group, and a carbamoylmethyl group.

The aromatic group may contain any of a nitro group, a halogen atom, an aliphatic oxy group, a carbamoyl group, an aliphatic oxycarbonyl group, an aliphatic thio group, an amino group, an aliphatic amino group, an acylamino group, a carbamoylamino group, and the like. Examples of the aromatic group include aryl groups containing six to twelve, preferably six to ten carbon atoms in total, such as a phenyl group, a 4-nitrophenyl group, a 4-acetylaminophenyl group, and a 4-methanesulfonylphenyl group.

The heterocyclic group may contain any of a halogen atom, a hydroxy group, an aliphatic oxy group, a carbamoyl group, an aliphatic oxycarbonyl group, an aliphatic thio group, an amino group, an aliphatic amino group, an acylamino group, a carbamoylamino group, and the like. Examples of the heterocyclic group include 5- or 6-membered heterocyclic groups containing two to twelve, preferably two to ten carbon atoms in total, such as a 2-tetrahydrofuryl group and a 2-pyrimidyl group.

The acyl group may contain any of an aliphatic carbonyl group, an arylcarbonyl group, a heterocyclic carbonyl group, a hydroxy group, a halogen atom, an aromatic group, an aliphatic oxy group, a carbamoyl group, an aliphatic oxycarbonyl group, an aliphatic thio group, an amino group, an aliphatic amino group, an acylamino group, a carbamoylamino group, and the like. Examples of the acyl group include acyl groups containing two to eight, preferably two to four carbon atoms in total, such as an acetyl group, a propanoyl group, a benzoyl group, and a 3-pyridinecarbonyl group.

The acylamino group may contain any of an aliphatic group, an aromatic group, a heterocyclic group, and the like, and may contain any of an acetylamino group, a benzoylamino group, a 2-pyridinecarbonylamino group, a propanoylamino group, and the like, for example. Examples of the acylamino group include acylamino groups containing two to twelve, preferably two to eight carbon atoms in total, and alkylcarbonylamino groups containing two to eight carbon atoms in total, such as an acetylamino group, a benzoylamino group, a 2-pyridinecarbonylamino group, and a propanoylamino group.

The aliphatic oxycarbonyl group may be either saturated or unsaturated, and may contain any of a hydroxy group, an aliphatic oxy group, a carbamoyl group, an aliphatic oxycarbonyl group, an aliphatic thio group, an amino group, an aliphatic amino group, an acylamino group, a carbamoylamino group, and the like. Examples of the aliphatic oxycarbonyl group include alkoxycarbonyl groups containing two to eight, preferably two to four carbon atoms in total, such as a methoxycarbonyl group, an ethoxycarbonyl group, and a (t)-butoxycarbonyl group.

The carbamoyl group may contain any of an aliphatic group, an aromatic group, a heterocyclic group, and the like. Examples of the carbamoyl group include an unsubstituted carbamoyl group and alkylcarbamoyl groups containing two to nine carbon atoms in total, preferably an unsubstituted carbamoyl group and alkylcarbamoyl groups containing two to five carbon atoms in total, such as a N-methylcarbamoyl group, a N,N-dimethylcarbamoyl group, and a N-phenylcarbamoyl group.

The aliphatic sulfonyl group may be either saturated or unsaturated, and may contain any of a hydroxy group, an aromatic group, an aliphatic oxy group, a carbamoyl group, an aliphatic oxycarbonyl group, an aliphatic thio group, an amino group, an aliphatic amino group, an acylamino group, a carbamoylamino group, and the like. Examples of the aliphatic sulfonyl group include alkyl sulfonyl groups containing one to six, preferably one to four carbon atoms in total, such as a methanesulfonyl group.

The aromatic sulfonyl group may contain any of a hydroxy group, an aliphatic group, an aliphatic oxy group, a carbamoyl group, an aliphatic oxycarbonyl group, an aliphatic thio group, an amino group, an aliphatic amino group, an acylamino group, a carbamoylamino group, and the like. Examples of the aromatic sulfonyl group include arylsulfonyl groups containing six to ten carbon atoms in total, such as a benzenesulfonyl group.

The amino group may contain any of an aliphatic group, an aromatic group, a heterocyclic group, and the like.

The acylamino group may contain any of an acetylamino group, a benzoylamino group, a 2-pyridinecarbonylamino group, a propanoylamino group, and the like. Examples of the acylamino group include acylamino groups containing two to twelve, preferably two to eight carbon atoms in total, more preferably alkylcarbonylamino groups containing two to eight carbon atoms in total, such as an acetylamino group, a benzoylamino group, a 2-pyridinecarbonylamino group, and a propanoylamino group.

The aliphatic sulfonamide group, the aromatic sulfonamide group, and the heterocyclic sulfonamide group may respectively be a methanesulfonamide group, a benzene sulfonamide group, and a 2-pyridinesulfonamide group, for example.

The sulfamoyl group may contain any of an aliphatic group, an aromatic group, a heterocyclic group, and the like. Examples of the sulfamoyl group include a sulfamoyl group, alkylsulfamoyl groups containing one to nine carbon atoms in total, dialkylsulfamoyl groups containing two to ten carbon atoms in total, arylsulfamoyl groups containing seven to thirteen carbon atoms in total, and heterocyclic sulfamoyl groups containing two to twelve carbon atoms in total, more preferably a sulfamoyl group, alkylsulfamoyl groups containing one to seven carbon atoms in total, dialkylsulfamoyl groups containing three to six carbon atoms in total, arylsulfamoyl groups containing six to eleven carbon atoms in total, and heterocyclic sulfamoyl groups containing two to ten carbon atoms in total, such as a sulfamoyl group, a methylsulfamoyl group, a N,N-dimethylsulfamoyl group, a phenylsulfamoyl group, and a 4-pyridinesulfamoyl group.

The aliphatic oxy group may be either saturated or unsaturated, and may contain any of a methoxy group, an ethoxy group, an i-propyloxy group, a cyclohexyloxy group, a methoxyethoxy group, and the like. Examples of the aliphatic oxy group include alkoxy groups containing one to eight, preferably one to six carbon atoms in total, such as a methoxy group, an ethoxy group, an i-propyloxy group, a cyclohexyloxy group, and a methoxyethoxy group.

The aromatic amino group and the heterocyclic amino group each may contain any of an aliphatic group, an aliphatic oxy group, a halogen atom, a carbamoyl group, a heterocyclic group ring-fused with the aryl group, and an aliphatic oxycarbonyl group, preferably any of an aliphatic group containing one to four carbon atoms in total, an aliphatic oxy group containing one to four carbon atoms in total, a halogen atom, a carbamoyl group containing one to four carbon atoms in total, a nitro group, and an aliphatic oxycarbonyl group containing two to four carbon atoms in total.

The aliphatic thio group may be either saturated or unsaturated, and examples thereof include alkylthio groups containing one to eight, more preferably one to six carbon atoms in total, such as a methylthio group, an ethylthio group, a carbamoylmethylthio group, and a t-butylthio group.

The carbamoylamino group may contain any of an aliphatic group, an aryl group, a heterocyclic group, and the like. Examples of the carbamoylamino group include a carbamoylamino group, alkylcarbamoylamino groups containing two to nine carbon atoms in total, dialkylcarbamoylamino groups containing three to ten carbon atoms in total, arylcarbamoylamino groups containing seven to thirteen carbon atoms in total, and heterocyclic carbamoylamino groups containing three to twelve carbon atoms in total, preferably a carbamoylamino group, alkylcarbamoylamino groups containing two to seven carbon atoms in total, dialkylcarbamoylamino groups containing three to six carbon atoms in total, arylcarbamoylamino groups containing seven to eleven carbon atoms in total, and heterocyclic carbamoylamino group containing three to ten carbon atoms in total, such as a carbamoylamino group, a methylcarbamoylamino group, a N,N-dimethylcarbamoylamino group, a phenylcarbamoylamino group, and a 4-pyridinecarbamoylamino group.

The invention relates to a compound represented by the following formula.

[Chem. 4]

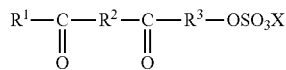

In the formula, $R^1$ is a linear or branched alkyl group containing one or more carbon atoms or a cyclic alkyl group containing three or more carbon atoms.

The alkyl group, when containing three or more carbon atoms, may optionally contain a carbonyl group (—C(=O)—) between two carbon atoms. The alkyl group, when containing two or more carbon atoms, may optionally contain a carbonyl group at an end of the alkyl group. In other words, acyl groups such as an acetyl group represented by $CH_3$—C(=O)— are also included in the alkyl group.

The alkyl group, when containing three or more carbon atoms, may optionally contain a monovalent or divalent heterocycle, or may optionally be in a cyclized form. The heterocycle is preferably an unsaturated heterocycle, more preferably an oxygen-containing unsaturated heterocycle, and may be a furan ring, for example. In $R^1$, a divalent heterocycle may be inserted between two carbon atoms, or a divalent heterocycle may be present at an end and bind to —C(=O)—, or a monovalent heterocycle may be present at an end of the alkyl group.

The alkyl group for $R^1$ may optionally contain a substituent. The substituent which may be contained in the alkyl group for $R^1$ is preferably a halogen atom, a C1-C10 linear or branched alkyl group, a C3-C10 cyclic alkyl group, or a hydroxy group, particularly preferably a methyl group or an ethyl group.

In the alkyl group, a hydrogen atom that binds to a carbon atom may optionally be replaced by a functional group such as a hydroxy group (—OH) or a monovalent organic group containing an ester bond. Still, it is preferably not replaced by any functional group.

An example of the monovalent organic group containing an ester bond is a group represented by the formula: —O—C(=O)—$R^{101}$, wherein $R^{101}$ is an alkyl group.

In the alkyl group, 75% or less of the hydrogen atoms binding to any carbon atom may be replaced by halogen atoms, 50% or less thereof may be replaced by halogen atoms, or 25% or less thereof may be replaced by halogen atoms. The alkyl group is preferably a non-halogenated alkyl group containing no halogen atoms such as fluorine atoms and chlorine atoms.

In the formula, $R^2$ and $R^3$ are each individually a single bond or a divalent linking group.

Preferably, $R^2$ and $R^3$ are each individually a single bond, a linear or branched alkylene group containing one or more carbon atoms, or a cyclic alkylene group containing three or more carbon atoms.

The alkylene group constituting $R^2$ and $R^3$ preferably contains no carbonyl group.

In the alkylene group, a hydrogen atom that binds to a carbon atom may optionally be replaced by a functional group such as a hydroxy group (—OH) or a monovalent organic group containing an ester bond. Still, it is preferably not replaced by any functional group.

An example of the monovalent organic group containing an ester bond is a group represented by the formula: —O—C(=O)—$R^{102}$ wherein $R^{102}$ is an alkyl group.

In the alkylene group, 75% or less of the hydrogen atoms binding to any carbon atom may be replaced by halogen atoms, 50% or less thereof may be replaced by halogen atoms, or 25% or less thereof may be replaced by halogen atoms. The alkylene group is preferably a non-halogenated alkylene group containing no halogen atoms such as fluorine atoms and chlorine atoms.

$R^1$, $R^2$, and $R^3$ contain 6 or more carbon atoms in total. The total number of carbon atoms is preferably 8 or greater, more preferably 9 or greater, still more preferably 10 or greater, while preferably 20 or smaller, more preferably 18 or smaller, still more preferably 15 or smaller.

Any two of $R^1$, $R^2$, and $R^3$ may optionally bind to each other to form a ring.

In the formula, X is H, a metal atom, $NR^4_4$, imidazolium optionally containing a substituent, pyridinium optionally containing a substituent, or phosphonium optionally containing a substituent, wherein $R^4$ is H or an organic group, and the four $R^4$s are the same as or different from each other. $R^4$ is preferably H or a C1-C10 organic group, more preferably H or a C1-C4 organic group. Examples of the metal atom include alkali metals (Group 1) and alkaline earth metals (Group 2), and Na, K, or Li is preferred.

X is preferably H, a metal atom, or $NR^4_4$, more preferably H, an alkali metal (Group 1), an alkaline earth metal (Group 2), or $NR^4_4$, still more preferably H, Na, K, Li, or $NH_4$, further more preferably Na, K, or $NH_4$, particularly preferably Na or $NH_4$, most preferably $NH_4$.

$R^1$ is preferably a C1-C8 linear or branched alkyl group containing no carbonyl group, a C3-C8 cyclic alkyl group containing no carbonyl group, a C2-C45 linear or branched alkyl group containing 1 to 10 carbonyl groups, a C3-C45 cyclic alkyl group containing a carbonyl group, or a C3-C45 alkyl group containing a monovalent or divalent heterocycle.

$R^1$ is more preferably a group represented by the following formula:

[Chem. 5]

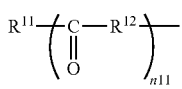

wherein n11 is an integer of 0 to 10; $R^{11}$ is a C1-C5 linear or branched alkyl group or a C3-C5 cyclic alkyl group; and $R^{12}$ is a C0-C3 alkylene group, and when n11 is an integer of 2 to 10, $R^{12}$s may be the same as or different from each other.

In the formula, n11 is preferably an integer of 0 to 5, more preferably an integer of 0 to 3, still more preferably an integer of 1 to 3.

The alkyl group for $R^{11}$ preferably contains no carbonyl group.

In the alkyl group for $R^{11}$, a hydrogen atom that binds to a carbon atom may optionally be replaced by a functional group such as a hydroxy group (—OH) or a monovalent organic group containing an ester bond. Still, it is preferably not replaced by any functional group.

An example of the monovalent organic group containing an ester bond is a group represented by the formula: —O—C(=O)—$R^{103}$, wherein $R^{103}$ is an alkyl group.

In the alkyl group for $R^{11}$, 75% or less of the hydrogen atoms binding to any carbon atom may be replaced by halogen atoms, 50% or less thereof may be replaced by halogen atoms, or 25% or less thereof may be replaced by halogen atoms. The alkyl group is preferably a non-halogenated alkyl group containing no halogen atoms such as fluorine atoms and chlorine atoms.

The alkyl group for $R^{11}$ may contain 1 to 20 carbon atoms. The number of carbon atoms is preferably 1 to 15, more preferably 1 to 12, still more preferably 1 to 10, further more preferably 1 to 8, still further more preferably 1 to 6, still much more preferably 1 to 3, particularly preferably 1 or 2, most preferably 1. The alkyl group for $R^{11}$ preferably consists only of any of primary carbons, secondary carbons, and tertiary carbons, particularly preferably consists only of any of primary carbons and secondary carbons. In other words, $R^{11}$ is preferably a methyl group, an ethyl group, a n-propyl group, or an isopropyl group, most preferably a methyl group.

$R^{11}$ is preferably a C1-C10 linear or branched alkyl group optionally containing a substituent or a C3-C10 cyclic alkyl group optionally containing a substituent, more preferably a C1-C10 linear or branched alkyl group containing no carbonyl group or a C3-C10 cyclic alkyl group containing no carbonyl group, still more preferably a C1-C10 linear or branched alkyl group containing no substituent, further more preferably a C1-C3 linear or branched alkyl group containing no substituent, particularly preferably a methyl group (—CH$_3$) or an ethyl group (—C$_2$H$_5$), most preferably a methyl group (—CH$_3$).

The alkyl group for $R^{11}$ may optionally contain a substituent. The substituent which may be contained in the alkyl group for $R^{11}$ is preferably a halogen atom, a C1-C10 linear or branched alkyl group, a C3-C10 cyclic alkyl group, or a hydroxy group, particularly preferably a methyl group or an ethyl group.

$R^{12}$ is a C0-C3 alkylene group. The number of carbon atoms is preferably 1 to 3.

The alkylene group for $R^{12}$ may be either linear or branched.

The alkylene group for $R^{12}$ preferably contains no carbonyl group. $R^{12}$ is more preferably an ethylene group (—C$_2$H$_4$—) or a propylene group (—C$_3$H$_6$—).

In the alkylene group, a hydrogen atom that binds to a carbon atom for $R^{12}$ may optionally be replaced by a functional group such as a hydroxy group (—OH) or a monovalent organic group containing an ester bond. Still, it is preferably not replaced by any functional group.

An example of the monovalent organic group containing an ester bond is a group represented by the formula: —O—C(=O)—$R^{104}$, wherein $R^{104}$ is an alkyl group.

In the alkylene group for $R^{12}$, 75% or less of the hydrogen atoms binding to any carbon atom may be replaced by halogen atoms, 50% or less thereof may be replaced by halogen atoms, or 25% or less thereof may be replaced by halogen atoms. The alkylene group is preferably a non-halogenated alkylene group containing no halogen atoms such as fluorine atoms and chlorine atoms.

$R^2$ and $R^3$ are each individually a linear or branched alkylene group containing no carbonyl group and containing one or more carbon atoms, more preferably a C1-C3 linear or branched alkylene group containing no carbonyl group, still more preferably an ethylene group (—C$_2$H$_4$—) or a propylene group (—C$_3$H$_6$—).

Examples of the above compound include the following compounds. In each formula, X is defined as mentioned above.

[Chem. 6]

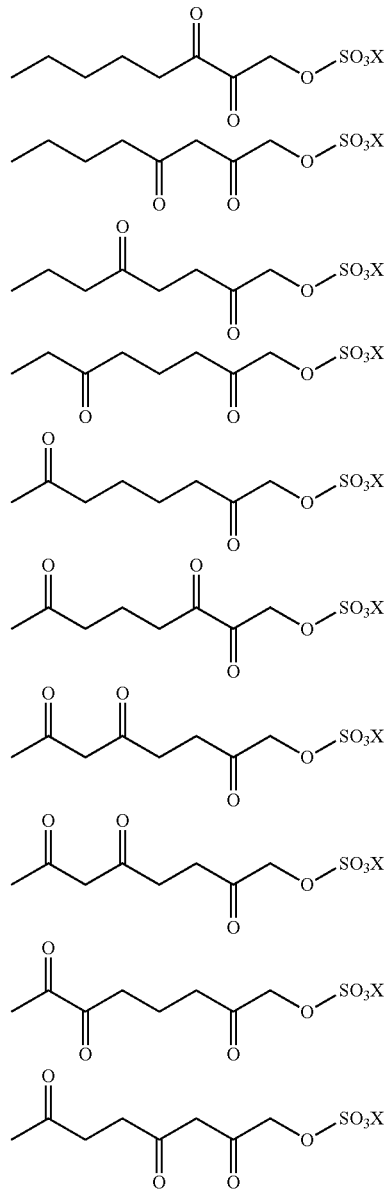

[Chem. 7]

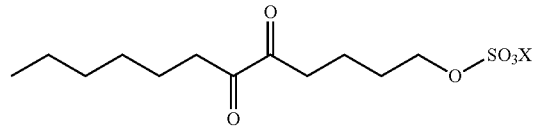

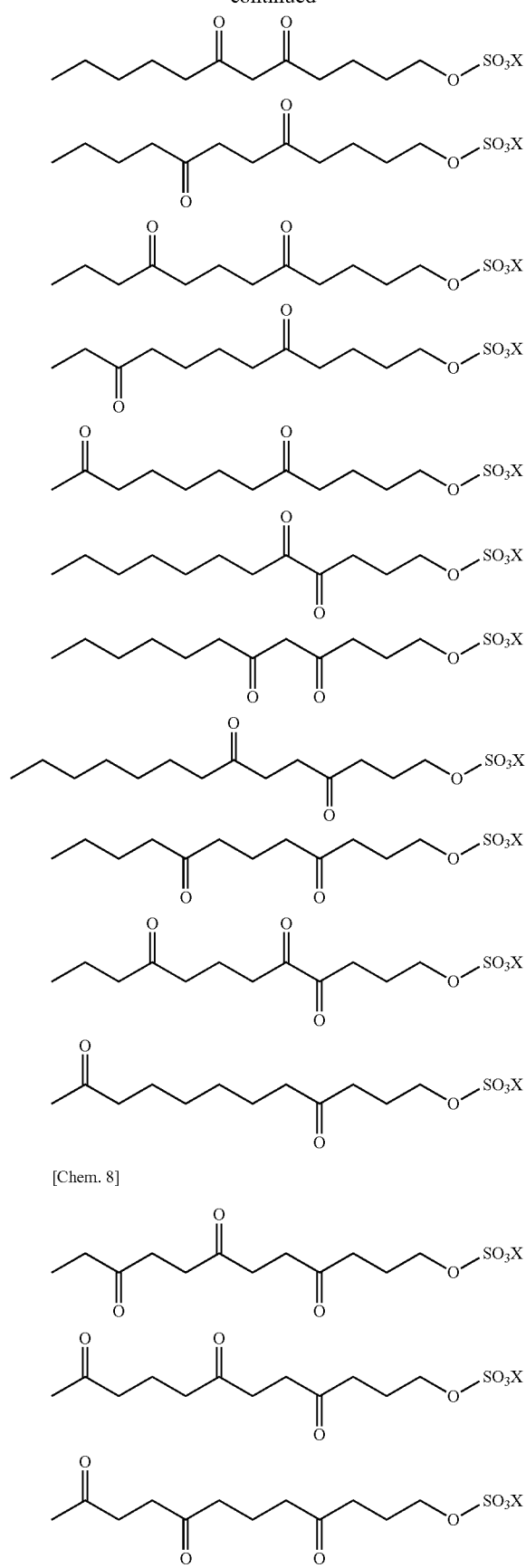
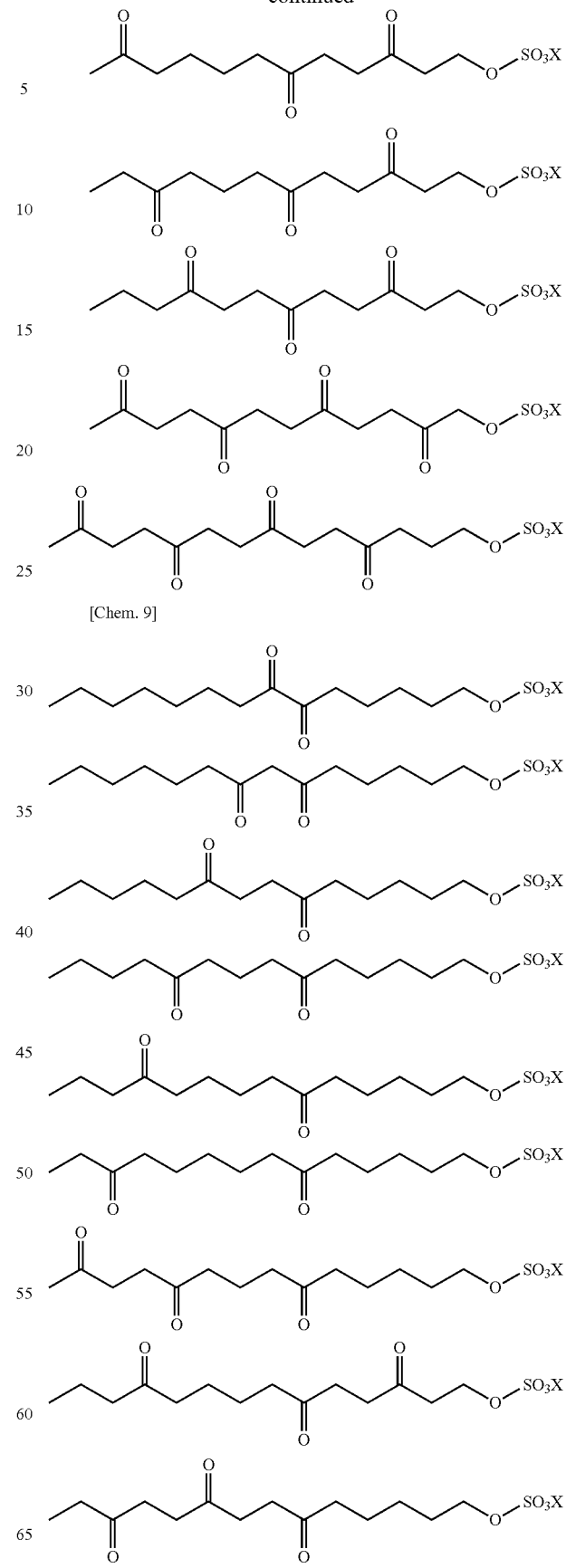

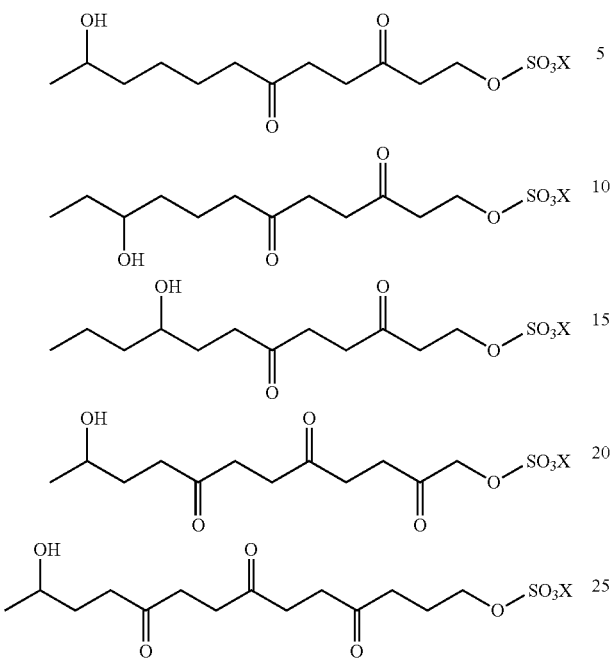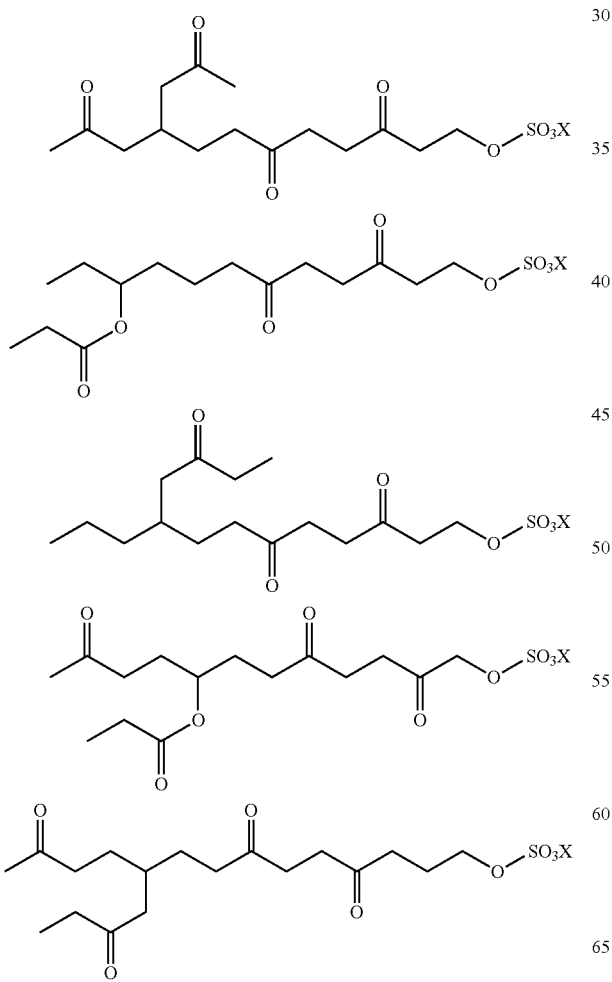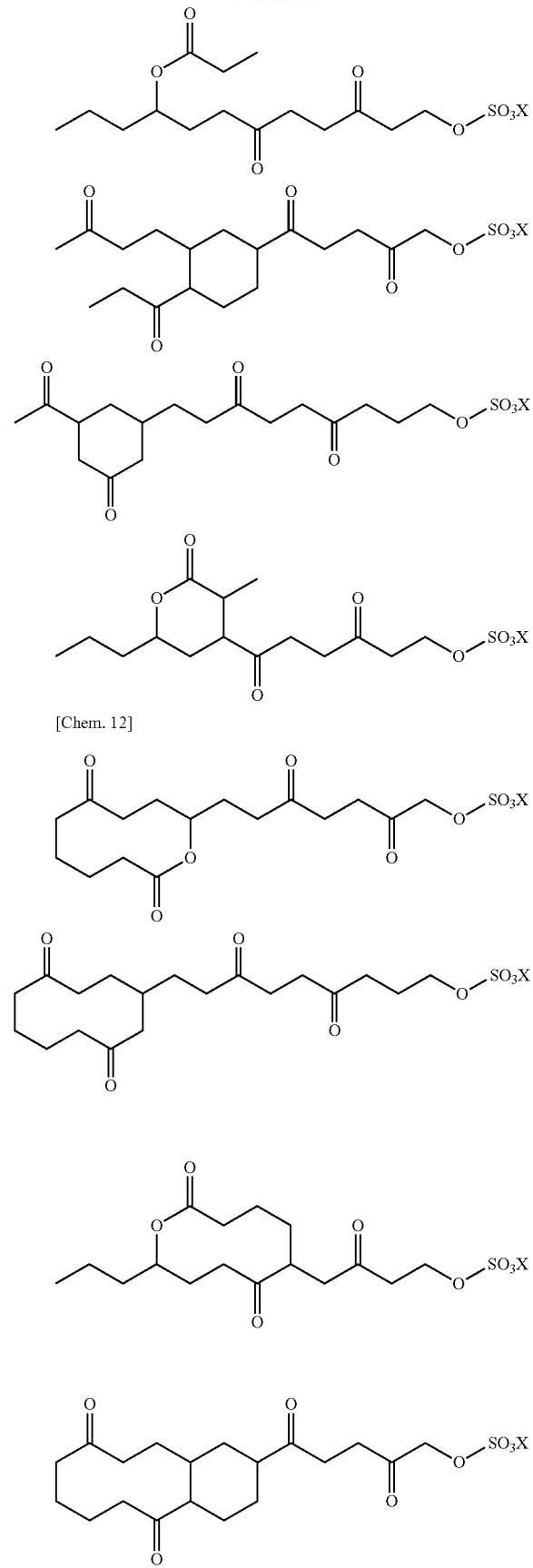

-continued

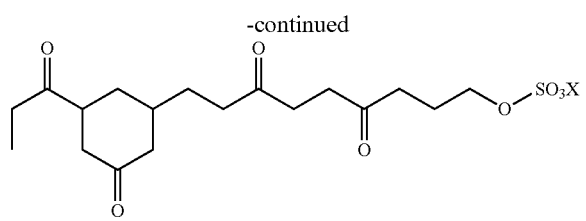
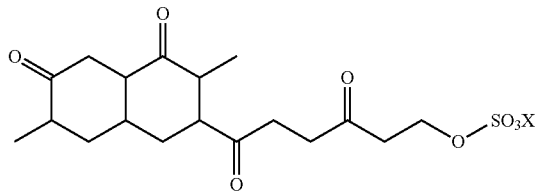

[Chem. 13]

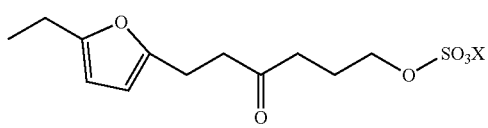
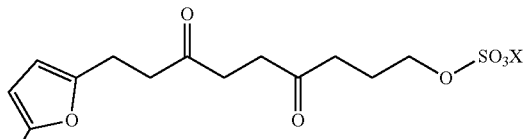
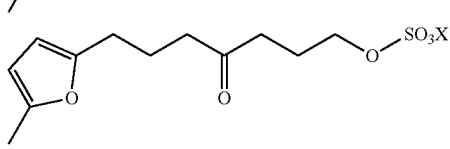
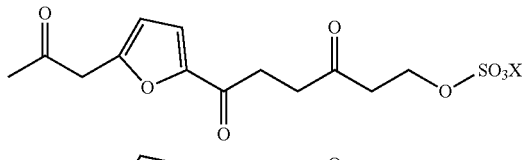
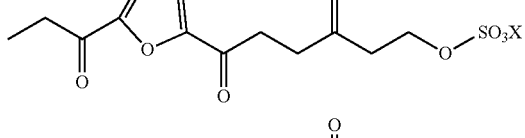
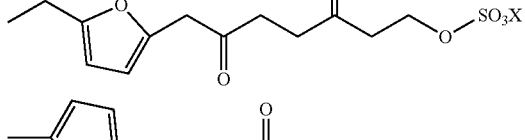
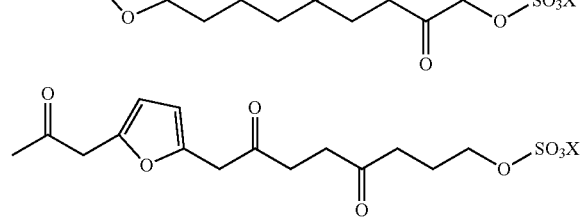
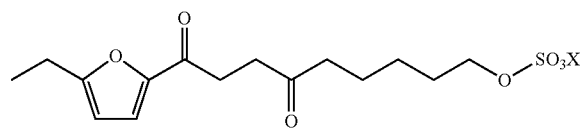

The compound of the invention may be produced by a production method including:

a step (11) of reacting a compound (10) represented by the following formula:

[Chem. 14]

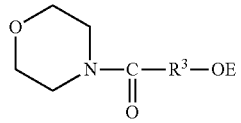

(wherein $R^3$ is defined as mentioned above; and E is a leaving group), lithium, and a chlorosilane compound represented by the formula: $R^{201}{}_3Si\text{-}Cl$ (wherein $R^{201}$s are each individually an alkyl group or an aryl group) to provide a compound (11) represented by the following formula:

[Chem. 15]

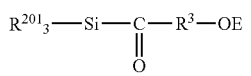

(wherein $R^3$, $R^{201}$, and E are defined as mentioned above);

a step (12) of reacting the compound (11) and an olefin represented by the following formula:

[Chem. 16]

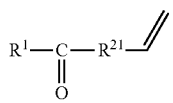

(wherein $R^1$ is defined as mentioned above; and $R^{21}$ is a single bond or a divalent linking group) to provide a compound (12) represented by the following formula:

[Chem. 17]

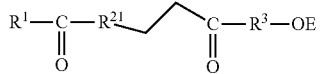

(wherein $R^1$, $R^{21}$, $R^3$, and E are defined as mentioned above);

a step (13) of eliminating the leaving group contained in the compound (12) to provide a compound (13) represented by the following formula:

[Chem. 18]

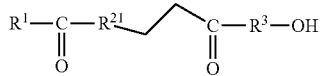

(wherein $R^1$, $R^{21}$, and $R^3$ are defined as mentioned above); and a step (14) of reacting the compound (13) and a chlorosulfonic acid represented by the following formula:

[Chem. 19]

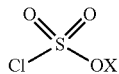

(wherein X is defined as mentioned above) to provide a compound (14) represented by the following formula:

[Chem. 20]

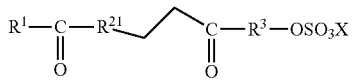

(wherein $R^1$, $^{21}$, $R^3$, and X are defined as mentioned above).

When $R^1$ contains a furan ring, the furan ring may be cleaved with an acid and converted into a dicarbonyl derivative, for example. Examples of the acid include acetic acid, hydrochloric acid, and p-toluenesulfonic acid. Acetic acid is preferred.

In the step (11), the compound (11) is preferably obtained by reacting lithium and the chlorosilane compound in advance to provide a siloxylithium compound, and then reacting this siloxylithium compound and the compound (10).

E represents a leaving group. Examples of the leaving group include a tert-butyldimethylsilyl (TBS) group, a triethylsilyl (TES) group, a triisopropylsilyl (TIPS) group, a tert-butyldiphenylsilyl (TBDPS) group, and a benzyl (Bn) group.

$R^{21}$ is preferably a single bond or a linear or branched alkylene group containing one or more carbon atoms.

Examples of the chlorosilane compound include the following.

[Chem. 21]

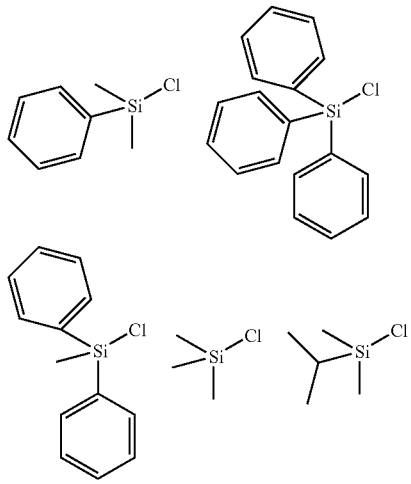

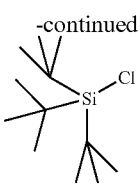

Any of the reactions in the step (11) may be performed in a solvent. The solvent is preferably an organic solvent, more preferably an aprotic polar solvent, still more preferably an ether. Examples of the ether include ethyl methyl ether, diethyl ether, monoglyme(ethylene glycol dimethyl ether), diglyme(diethylene glycol dimethyl ether), triglyme(triethylene glycol dimethyl ether), tetrahydrofuran, tetraglyme (tetraethylene glycol dimethyl ether), and crown ethers (e.g., 15-crown-5, 18-crown-6). Tetrahydrofuran and diethyl ether are preferred.

The temperature of the reaction between lithium and the chlorosilane compound in the step (11) is preferably −78° C. to 150° C., more preferably 0° C. to 100° C., still more preferably 10° C. to 40° C., particularly preferably 20° C. to 30° C.

The temperature of the reaction between the siloxylithium compound and the compound (10) in the step (11) is preferably −100° C. to 0° C., more preferably −80° C. to −50° C., while preferably −100° C. to 100° C., more preferably −80° C. to 50° C.

The pressure of the reaction between lithium and the chlorosilane compound in the step (11) is preferably 0.1 to 5 MPa, more preferably 0.1 to 1 MPa.

The pressure of the reaction between the siloxylithium compound and the compound (10) in the step (11) is preferably 0.1 to 5 MPa, more preferably 0.1 to 1 MPa.

The duration of the reaction between lithium and the chlorosilane compound in the step (11) is preferably 0.1 to 72 hours, more preferably 1 to 48 hours, still more preferably 6 to 10 hours.

The duration of the reaction between the siloxylithium compound and the compound (10) in the step (11) is preferably 0.1 to 72 hours, more preferably 1 to 2 hours.

For the reaction ratio between the compound (11) and the olefin in the step (12), the amount of the olefin is preferably 0.5 to 10 mol, more preferably 1 to 2 mol, still more preferably 0.6 to 5.0 mol, particularly preferably 1 to 1.1 mol, relative to 1 mol of the compound (11), so as to improve the yield and to reduce the waste.

The reaction in the step (12) may be performed in a solvent in the presence of a thiazolium salt or a base.

Examples of the thiazolium salt include 3-ethyl-5-(2-hydroxyethyl)-4-methylthiazolium bromide and 3-benzyl-5-(2-hydroxyethyl)-4-methylthiazolium chloride.

Examples of the base include 1,8-diazabicyclo[5.4.0]-7-undecene and triethylamine.

The solvent is preferably an organic solvent, more preferably an aprotic polar solvent, still more preferably an alcohol or an ether.

Examples of the alcohol include methanol, ethanol, 1-propanol, and isopropanol.

Examples of the ether include ethyl methyl ether, diethyl ether, monoglyme(ethylene glycol dimethyl ether), diglyme (diethylene glycol dimethyl ether), triglyme(triethylene glycol dimethyl ether), tetrahydrofuran, tetraglyme(tetraethylene glycol dimethyl ether), and crown ethers (e.g., 15-crown-5, 18-crown-6). Tetrahydrofuran and diethyl ether are preferred.

The reaction temperature in the step (12) is preferably −78° C. to 150° C., more preferably 0° C. to 100° C., still more preferably 40° C. to 60° C., particularly preferably 50° C. to 55° C.

The reaction pressure in the step (12) is preferably 0.1 to 5 MPa, more preferably 0.1 to 1 MPa.

The reaction duration in the step (12) is preferably 0.1 to 72 hours, more preferably 1 to 48 hours, still more preferably 6 to 10 hours.

The elimination reaction for the leaving group in the step (13) may be performed using a fluoride ion or an acid. Examples of methods of eliminating the leaving group include a method of using hydrofluoric acid; a method of using an amine complex of hydrogen fluoride such as pyridine-nHF or triethylamine-nHF; a method of using an inorganic salt such as cesium fluoride, potassium fluoride, lithium tetrafluoroborate ($LiBF_4$), or ammonium fluoride; and a method of using an organic salt such as tetrabutylammonium fluoride (TBAF).

The elimination reaction for the leaving group in the step (13) may be performed in a solvent. The solvent is preferably an organic solvent, more preferably an aprotic polar solvent, still more preferably an ether.

Examples of the ether include ethyl methyl ether, diethyl ether, monoglyme(ethylene glycol dimethyl ether), diglyme (diethylene glycol dimethyl ether), triglyme(triethylene glycol dimethyl ether), tetrahydrofuran, tetraglyme(tetraethylene glycol dimethyl ether), and crown ethers (e.g., 15-crown-5, 18-crown-6). Tetrahydrofuran and diethyl ether are preferred.

The reaction temperature in the step (13) is preferably −78° C. to 150° C., more preferably 0° C. to 100° C., still more preferably 0° C. to 40° C., particularly preferably 0° C. to 20° C.

The reaction pressure in the step (13) is preferably 0.1 to 5 MPa, more preferably 0.1 to 1 MPa.

The reaction duration in the step (13) is preferably 0.1 to 72 hours, more preferably 1 to 48 hours, still more preferably 3 to 8 hours.

For the reaction ratio between the compound (13) and the chlorosulfonic acid in the step (14), the amount of the chlorosulfonic acid is preferably 0.5 to 10.0 mol, more preferably 0.6 to 5.0 mol, still more preferably 1 to 2 mol, particularly preferably 1 to 1.1 mol, relative to 1 mol of the compound (13), so as to improve the yield and to reduce the waste.

The reaction in the step (14) is preferably performed in the presence of a base. Examples of the base include alkali metal hydroxides, alkaline earth metal hydroxides, and amines. Amines are preferred.

Examples of the amines in the step (14) include tertiary amines such as trimethylamine, triethylamine, tributylamine, N,N-dimethylaniline, dimethylbenzylamine, and N,N,N',N'-tetramethyl-1,8-naphthalenediamine, heteroaromatic amines such as pyridine, pyrrole, uracil, collidine, and lutidine, and cyclic amines such as 1,8-diaza-bicyclo[5.4.0]-7-undecene and 1,5-diaza-bicyclo[4.3.0]-5-nonene. Triethylamine and pyridine are preferred.

In order to improve the yield and to reduce the waste, the amount of the base used in the step (14) is preferably 0.5 to 10 mol, more preferably 0.6 to 5.0 mol, still more preferably 1 to 2 mol, particularly preferably 1 to 1.1 mol, relative to 1 mol of the compound (13).

The reaction in the step (14) may be performed in a polar solvent. The solvent is preferably an organic solvent, more preferably an aprotic polar solvent, still more preferably an ether.

Examples of the ether include ethyl methyl ether, diethyl ether, monoglyme(ethylene glycol dimethyl ether), diglyme (diethylene glycol dimethyl ether), triglyme(triethylene glycol dimethyl ether), tetrahydrofuran, tetraglyme(tetraethylene glycol dimethyl ether), and crown ethers (e.g., 15-crown-5, 18-crown-6). Diethyl ether is preferred.

The reaction temperature in the step (14) is preferably −78° C. to 150° C., more preferably 0° C. to 100° C., still more preferably 0° C. to 40° C., particularly preferably 0° C. to 20° C.

The reaction pressure in the step (14) is preferably 0.1 to 5 MPa, more preferably 0.1 to 1 MPa.

The reaction duration in the step (14) is preferably 0.1 to 72 hours, more preferably 1 to 48 hours, still more preferably 3 to 12 hours.

The reaction in the step (14) performed in a solvent can provide a solution containing the compound (14) after completion of the reaction. Optionally, the compound (14) at high purity may be collected therefrom by adding water to the solution, leaving the mixture to stand and thereby separating the mixture into two phases, collecting the aqueous phase, and evaporating the solvent. When the compound (14) contains a group represented by —$OSO_3H$ (i.e., when X is H), an alkaline aqueous solution such as a sodium hydrogen carbonate aqueous solution or ammonia water may be used instead of water to convert the —$OSO_3H$ group into a sulfuric acid salt group.

The resulting compounds may be subjected to any of evaporation of a solvent or operations such as distillation and purification after the respective steps, whereby the purity of each compound may be increased.

The compound of the invention may also be produced by a production method including:

a step (21) of reacting a ketone represented by the following formula:

[Chem. 22]

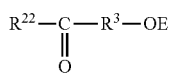

(wherein $R^3$ is defined as mentioned above; $R^{22}$ is a monovalent organic group; and E is a leaving group) and a carboxylate represented by the following formula:

[Chem. 23]

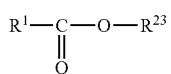

(wherein $R^1$ is defined as mentioned above; and $R^{23}$ is a monovalent organic group) to provide a compound (21) represented by the following formula:

[Chem. 24]

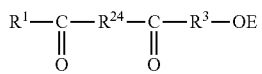

(wherein $R^1$, $R^3$, and E are defined as mentioned above; and $R^{24}$ is a single bond or a divalent linking group);

a step (22) of eliminating the leaving group in the compound (21) to provide a compound (22) represented by the following formula:

[Chem. 25]

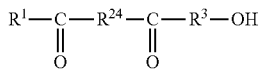

(wherein $R^1$, $R^{24}$, and $R^3$ are defined as mentioned above); and a step (23) of reacting the compound (22) and a chlorosulfonic acid represented by the following formula:

[Chem. 26]

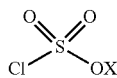

(wherein X is defined as mentioned above) to provide a compound (23) represented by the following formula:

[Chem. 27]

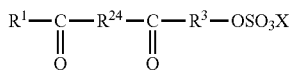

(wherein $R^1$, $R^{24}$, $R^3$, and X are defined as mentioned above).

When $R^1$ contains a furan ring, the furan ring may be cleaved with an acid and converted into a dicarbonyl derivative, for example. Examples of the acid include acetic acid, hydrochloric acid, and p-toluenesulfonic acid. Acetic acid is preferred.

E represents a leaving group. Examples of the leaving group include a tert-butyldimethylsilyl (TBS) group, a triethylsilyl (TES) group, a triisopropylsilyl (TIPS) group, a tert-butyldiphenylsilyl (TBDPS) group, and a benzyl (Bn) group.

$R^{22}$ is preferably a linear or branched alkyl group containing one or more carbon atoms, more preferably a methyl group.

$R^{23}$ is preferably a linear or branched alkyl group containing one or more carbon atoms, more preferably a methyl group.

$R^{24}$ is preferably a linear or branched alkylene group containing one or more carbon atoms, more preferably a methylene group (—$CH_2$—).

The reaction in the step (21) may be performed in a solvent in the presence of a base.

Examples of the base include sodium amide, sodium hydride, sodium methoxide, and sodium ethoxide.

The solvent is preferably an organic solvent, more preferably an aprotic polar solvent, still more preferably an alcohol or an ether.

Examples of the alcohol include methanol, ethanol, propanol, and isopropanol.

Examples of the ether include ethyl methyl ether, diethyl ether, monoglyme(ethylene glycol dimethyl ether), diglyme (diethylene glycol dimethyl ether), triglyme(triethylene glycol dimethyl ether), tetrahydrofuran, tetraglyme(tetraethylene glycol dimethyl ether), and crown ethers (e.g., 15-crown-5, 18-crown-6). Tetrahydrofuran and diethyl ether are preferred.

The reaction temperature in the step (21) is preferably —78° C. to 150° C., more preferably 0° C. to 100° C., still more preferably 0° C. to 40° C., particularly preferably 0° C. to 20° C.

The reaction pressure in the step (21) is preferably 0.1 to 5 MPa, more preferably 0.1 to 1 MPa.

The reaction duration in the step (21) is preferably 0.1 to 72 hours, more preferably 1 to 48 hours, still more preferably 3 to 8 hours.

The elimination reaction for the leaving group in the step (22) may be performed using a fluoride ion or an acid. Examples of methods of eliminating the leaving group include a method of using hydrofluoric acid; a method of using an amine complex of hydrogen fluoride such as pyridine-nHF or triethylamine-nHF; a method of using an inorganic salt such as cesium fluoride, potassium fluoride, lithium tetrafluoroborate ($LiBF_4$), or ammonium fluoride; and a method of using an organic salt such as tetrabutylammonium fluoride (TBAF).

The elimination reaction for the leaving group in the step (22) may be performed in a solvent. The solvent is preferably an organic solvent, more preferably an aprotic polar solvent, still more preferably an ether.

Examples of the ether include ethyl methyl ether, diethyl ether, monoglyme(ethylene glycol dimethyl ether), diglyme (diethylene glycol dimethyl ether), triglyme(triethylene glycol dimethyl ether), tetrahydrofuran, tetraglyme(tetraethylene glycol dimethyl ether), and crown ethers (e.g., 15-crown-5, 18-crown-6). Tetrahydrofuran and diethyl ether are preferred.

The reaction temperature in the step (22) is preferably –78° C. to 150° C., more preferably 0° C. to 100° C., still more preferably 0° C. to 40° C., particularly preferably 0° C. to 20° C.

The reaction pressure in the step (22) is preferably 0.1 to 5 MPa, more preferably 0.1 to 1 MPa.

The reaction duration in the step (22) is preferably 0.1 to 72 hours, more preferably 1 to 48 hours, still more preferably 3 to 8 hours.

For the reaction ratio between the compound (22) and the chlorosulfonic acid in the step (23), the amount of the chlorosulfonic acid is preferably 0.5 to 10.0 mol, more preferably 0.6 to 5.0 mol, still more preferably 1 to 2 mol, particularly preferably 1 to 1.1 mol, relative to 1 mol of the compound (22), so as to improve the yield and to reduce the waste.

The reaction in the step (23) is preferably performed in the presence of a base. Examples of the base include alkali metal hydroxides, alkaline earth metal hydroxides, and amines. Amines are preferred.

Examples of the amines in the step (23) include tertiary amines such as trimethylamine, triethylamine, tributylamine, N,N-dimethylaniline, dimethylbenzylamine, and N,N,N',N'-tetramethyl-1,8-naphthalenediamine, heteroaromatic amines such as pyridine, pyrrole, uracil, collidine, and lutidine, and cyclic amines such as 1,8-diaza-bicyclo[5.4.0]-7-undecene and 1,5-diaza-bicyclo[4.3.0]-5-nonene. Triethylamine and pyridine are preferred.

In order to improve the yield and to reduce the waste, the amount of the base used in the step (23) is preferably 0.5 to 10 mol, more preferably 0.6 to 5.0 mol, still more preferably 1 to 2 mol, particularly preferably 1 to 1.1 mol, relative to 1 mol of the compound (22).

The reaction in the step (23) may be performed in a polar solvent. The solvent is preferably an organic solvent, more preferably an aprotic polar solvent, still more preferably an ether.

Examples of the ether include ethyl methyl ether, diethyl ether, monoglyme(ethylene glycol dimethyl ether), diglyme (diethylene glycol dimethyl ether), triglyme(triethylene glycol dimethyl ether), tetrahydrofuran, tetraglyme(tetraethylene glycol dimethyl ether), and crown ethers (e.g., 15-crown-5, 18-crown-6). Diethyl ether is preferred.

The reaction temperature in the step (23) is preferably −78° C. to 150° C., more preferably 0° C. to 100° C., still more preferably 0° C. to 40° C., particularly preferably 0° C. to 20° C.

The reaction pressure in the step (23) is preferably 0.1 to 5 MPa, more preferably 0.1 to 1 MPa.

The reaction duration in the step (23) is preferably 0.1 to 72 hours, more preferably 1 to 48 hours, still more preferably 3 to 12 hours.

The reaction in the step (23) performed in a solvent can provide a solution containing the compound (23) after completion of the reaction. Optionally, the compound (23) at high purity may be collected therefrom by adding water to the solution, leaving the mixture to stand and thereby separating the mixture into two phases, collecting the aqueous phase, and evaporating the solvent. When the compound (23) contains a group represented by —OSO$_3$H (i.e., when X is H), an alkaline aqueous solution such as a sodium hydrogen carbonate aqueous solution or ammonia water may be used instead of water to convert the —OSO$_3$H group into a sulfuric acid salt group.

The resulting compounds may be subjected to any of evaporation of a solvent or operations such as distillation and purification after the respective steps, whereby the purity of each compound may be increased.

The compound of the invention may also be produced by a method including:

a step (31) of reacting an alkyl halide represented by the following formula:

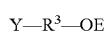

(wherein R$^3$ is defined as mentioned above; Y is a halogen atom; and E is a leaving group) and lithium acetylide represented by the following formula:

[Chem. 28]

(wherein R$^1$ is defined as mentioned above) to provide a compound (31) represented by the following formula:

[Chem. 29]

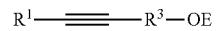

(wherein R$^1$, R$^3$, and E are defined as mentioned above);

a step (32) of oxidizing the compound (31) to provide a compound (32) represented by the following formula:

[Chem. 30]

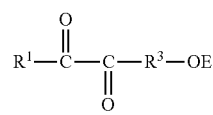

(wherein R$^1$, R$^3$, and E are defined as mentioned above);

a step (33) of eliminating the leaving group in the compound (32) to provide a compound (33) represented by the following formula:

[Chem. 31]

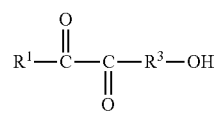

(wherein R$^1$ and R$^3$ are defined as mentioned above); and a step (34) of reacting the compound (33) and a chlorosulfonic acid represented by the following formula:

[Chem. 32]

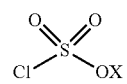

(wherein X is defined as mentioned above) to provide a compound (34) represented by the following formula:

[Chem. 33]

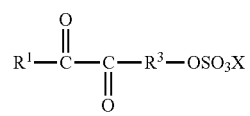

(wherein R$^1$, R$^3$, and X are defined as mentioned above).

When R$^1$ contains a furan ring, the furan ring may be cleaved with an acid and converted into a dicarbonyl derivative, for example. Examples of the acid include acetic acid, hydrochloric acid, and p-toluenesulfonic acid. Acetic acid is preferred.

E represents a leaving group. Examples of the leaving group include a tert-butyldimethylsilyl (TBS) group, a triethylsilyl (TES) group, a triisopropylsilyl (TIPS) group, a tert-butyldiphenylsilyl (TBDPS) group, and a benzyl (Bn) group.

For the reaction ratio between the alkyl halide and the lithium acetylide in the step (31), the amount of the lithium acetylide is preferably 0.5 to 10 mol, more preferably 0.6 to 5.0 mol, still more preferably 1 to 2 mol, particularly preferably 1 to 1.2 mol, relative to 1 mol of the alkyl halide, so as to improve the yield and to reduce the waste.

The reaction in the step (31) may be performed in a solvent. The solvent is preferably hexane.

The reaction temperature in the step (31) is preferably −100° C. to −40° C., more preferably −80° C. to −50° C., while preferably −100° C. to 100° C., more preferably −80° C. to 50° C.

The reaction pressure in the step (31) is preferably 0.1 to 5 MPa, more preferably 0.1 to 1 MPa.

The reaction duration in the step (31) is preferably 0.1 to 72 hours, more preferably 1 to 48 hours, still more preferably 6 to 10 hours.

The oxidation in the step (32) may be performed in a nitrile solvent using a complex generated by treating [(Cn*)Ru$^{III}$(CF$_3$CO$_2$)$_3$]·H$_2$O (wherein Cn* is 1,4,7-trimethyl-1,4,7-triazabicyclononane) with (NH$_4$)$_2$Ce(NO$_3$)$_6$ and trifluoroacetic acid and then adding sodium perchlorate thereto.

After the oxidation is completed, the product may be neutralized with an alkali, and then an organic solvent such as an ether may be used to extract the compound (32).

The reaction temperature in the step (32) is preferably −78° C. to 150° C., more preferably 0° C. to 100° C., still more preferably 30° C. to 100° C., particularly preferably 40° C. to 90° C.

The reaction pressure in the step (32) is preferably 0.1 to 5 MPa, more preferably 0.1 to 1 MPa.

The reaction duration in the step (32) is preferably 0.1 to 72 hours, more preferably 1 to 48 hours, still more preferably 3 to 8 hours.

The elimination reaction for the leaving group in the step (33) may be performed using a fluoride ion or an acid. Examples of methods of eliminating the leaving group include a method of using hydrofluoric acid; a method of using an amine complex of hydrogen fluoride such as pyridine-nHF or triethylamine-nHF; a method of using an inorganic salt such as cesium fluoride, potassium fluoride, lithium tetrafluoroborate (LiBF$_4$), or ammonium fluoride; and a method of using an organic salt such as tetrabutylammonium fluoride (TBAF).

The elimination reaction for the leaving group in the step (33) may be performed in a solvent. The solvent is preferably an organic solvent, more preferably an aprotic polar solvent, still more preferably an ether.

Examples of the ether include ethyl methyl ether, diethyl ether, monoglyme(ethylene glycol dimethyl ether), diglyme (diethylene glycol dimethyl ether), triglyme(triethylene glycol dimethyl ether), tetrahydrofuran, tetraglyme(tetraethylene glycol dimethyl ether), and crown ethers (e.g., 15-crown-5, 18-crown-6). Tetrahydrofuran and diethyl ether are preferred.

The reaction temperature in the step (33) is preferably −78° C. to 150° C., more preferably 0° C. to 100° C., still more preferably 0° C. to 40° C., particularly preferably 0° C. to 20° C.

The reaction pressure in the step (33) is preferably 0.1 to 5 MPa, more preferably 0.1 to 1 MPa.

The reaction duration in the step (33) is preferably 0.1 to 72 hours, more preferably 1 to 48 hours, still more preferably 3 to 8 hours.

For the reaction ratio between the compound (33) and the chlorosulfonic acid in the step (34), the amount of the chlorosulfonic acid is preferably 0.5 to 10.0 mol, more preferably 0.6 to 5.0 mol, still more preferably 1 to 2 mol, particularly preferably 1 to 1.1 mol, relative to 1 mol of the compound (33), so as to improve the yield and to reduce the waste.

The reaction in the step (34) is preferably performed in the presence of a base. Examples of the base include alkali metal hydroxides, alkaline earth metal hydroxides, and amines. Amines are preferred.

Examples of the amines in the step (34) include tertiary amines such as trimethylamine, triethylamine, tributylamine, N,N-dimethylaniline, dimethylbenzylamine, and N,N,N',N'-tetramethyl-1,8-naphthalenediamine, heteroaromatic amines such as pyridine, pyrrole, uracil, collidine, and lutidine, and cyclic amines such as 1,8-diaza-bicyclo[5.4.0]-7-undecene and 1,5-diaza-bicyclo[4.3.0]-5-nonene. Triethylamine and pyridine are preferred.

In order to improve the yield and to reduce the waste, the amount of the base used in the step (34) is preferably 0.5 to 10 mol, more preferably 0.6 to 5.0 mol, still more preferably 1 to 2 mol, particularly preferably 1 to 1.1 mol, relative to 1 mol of the compound (33).

The reaction in the step (34) may be performed in a polar solvent. The solvent is preferably an organic solvent, more preferably an aprotic polar solvent, still more preferably an ether.

Examples of the ether include ethyl methyl ether, diethyl ether, monoglyme(ethylene glycol dimethyl ether), diglyme (diethylene glycol dimethyl ether), triglyme(triethylene glycol dimethyl ether), tetrahydrofuran, tetraglyme(tetraethylene glycol dimethyl ether), and crown ethers (e.g., 15-crown-5, 18-crown-6). Diethyl ether is preferred.

The reaction temperature in the step (34) is preferably −78° C. to 150° C., more preferably 0° C. to 100° C., still more preferably 0° C. to 40° C., particularly preferably 0° C. to 20° C.

The reaction pressure in the step (34) is preferably 0.1 to 5 MPa, more preferably 0.1 to 1 MPa.

The reaction duration in the step (34) is preferably 0.1 to 72 hours, more preferably 1 to 48 hours, still more preferably 3 to 12 hours.

The reaction in the step (34) performed in a solvent can provide a solution containing the compound (34) after completion of the reaction. Optionally, the compound (34) at high purity may be collected therefrom by adding water to the solution, leaving the mixture to stand and thereby separating the mixture into two phases, collecting the aqueous phase, and evaporating the solvent. When the compound (34) contains a group represented by —OSO$_3$H (i.e., when X is H), an alkaline aqueous solution such as a sodium hydrogen carbonate aqueous solution or ammonia water may be used instead of water to convert the —OSO$_3$H group into a sulfuric acid salt group.

The resulting compounds may be subjected to any of evaporation of a solvent or operations such as distillation and purification after the respective steps, whereby the purity of each compound may be increased.

The compound of the invention may also be produced by a production method including:

a step (41) of reacting an alkene represented by the following formula:

[Chem. 34]

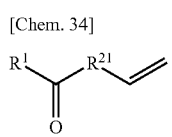

(wherein $R^1$ is defined as mentioned above; and $R^{21}$ is a single bond or a divalent linking group) and an alkyne represented by the following formula:

[Chem. 35]

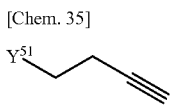

(wherein $Y^{51}$ is an alkoxy group) to provide a compound (41) represented by the following formula:

[Chem. 36]

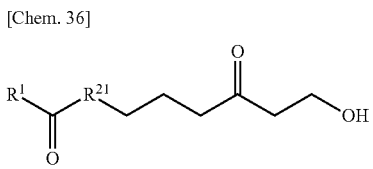

(wherein $R^1$ and $R^{21}$ are defined as mentioned above); and
a step (42) of reacting the compound (41) and a chlorosulfonic acid represented by the following formula:

[Chem. 37]

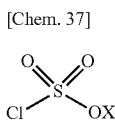

(wherein X is defined as mentioned above) to provide a compound (42) represented by the following formula:

[Chem. 38]

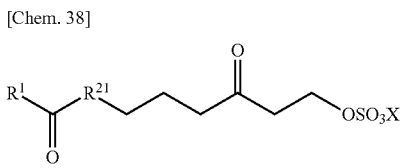

(wherein $R^1$, $R^{21}$, and X are defined as mentioned above).

When $R^1$ contains a furan ring, the furan ring may be cleaved with an acid and converted into a dicarbonyl derivative, for example. Examples of the acid include acetic acid, hydrochloric acid, and p-toluenesulfonic acid. Acetic acid is preferred.

$R^{21}$ is preferably a single bond or a linear or branched alkylene group containing one or more carbon atoms.

For the reaction ratio between the alkene and the alkyne in the step (41), the amount of the alkene is preferably 0.5 to 10 mol, more preferably 0.6 to 5.0 mol, still more preferably 0.5 to 2 mol, particularly preferably 0.6 to 1.2 mol, relative to 1 mol of the alkyne, so as to improve the yield and to reduce the waste.

The reaction in the step (41) is preferably performed in the presence of a metal catalyst. An example of the metal is ruthenium.

In order to improve the yield and to reduce the waste, the amount of the metal catalyst used in the step (41) is preferably 0.00001 to 0.4 mol, more preferably 0.00005 to 0.1 mol, still more preferably 0.01 to 0.4 mol, particularly preferably 0.05 to 0.1 mol, relative to 1 mol of the alkene.

The reaction in the step (41) may be performed in a polar solvent. The solvent is preferably water, acetonitrile, dimethylacetamide, or dimethylformamide.

The reaction temperature in the step (41) is preferably 20° C. to 160° C., more preferably 40° C. to 140° C.

The reaction pressure in the step (41) is preferably 0.1 to 5 MPa, more preferably 0.1 to 1 MPa.

The reaction duration in the step (41) is preferably 0.1 to 72 hours, more preferably 1 to 48 hours, still more preferably 4 to 8 hours.

For the reaction ratio between the compound (41) and the chlorosulfonic acid in the step (42), the amount of the chlorosulfonic acid is preferably 0.5 to 10.0 mol, more preferably 0.6 to 5.0 mol, still more preferably 1 to 2 mol, particularly preferably 1 to 1.1 mol, relative to 1 mol of the compound (41), so as to improve the yield and to reduce the waste.

The reaction in the step (42) is preferably performed in the presence of a base. Examples of the base include alkali metal hydroxides, alkaline earth metal hydroxides, and amines. Amines are preferred.

Examples of the amines in the step (42) include tertiary amines such as trimethylamine, triethylamine, tributylamine, N,N-dimethylaniline, dimethylbenzylamine, and N,N,N',N'-tetramethyl-1,8-naphthalenediamine, heteroaromatic amines such as pyridine, pyrrole, uracil, collidine, and lutidine, and cyclic amines such as 1,8-diaza-bicyclo[5.4.0]-7-undecene and 1,5-diaza-bicyclo[4.3.0]-5-nonene. Triethylamine and pyridine are preferred.

In order to improve the yield and to reduce the waste, the amount of the base used in the step (42) is preferably 0.5 to 10 mol, more preferably 0.6 to 5.0 mol, still more preferably 1 to 2 mol, particularly preferably 1 to 1.1 mol, relative to 1 mol of the compound (41).

The reaction in the step (42) may be performed in a polar solvent. The solvent is preferably an organic solvent, more preferably an aprotic polar solvent, still more preferably an ether.

Examples of the ether include ethyl methyl ether, diethyl ether, monoglyme(ethylene glycol dimethyl ether), diglyme (diethylene glycol dimethyl ether), triglyme(triethylene glycol dimethyl ether), tetrahydrofuran, tetraglyme(tetraethylene glycol dimethyl ether), and crown ethers (e.g., 15-crown-5, 18-crown-6). Diethyl ether is preferred.

The reaction temperature in the step (42) is preferably −78° C. to 150° C., more preferably 0° C. to 100° C., still more preferably 0° C. to 40° C., particularly preferably 0° C. to 20° C.

The reaction pressure in the step (42) is preferably 0.1 to 5 MPa, more preferably 0.1 to 1 MPa.

The reaction duration in the step (42) is preferably 0.1 to 72 hours, more preferably 1 to 48 hours, still more preferably 3 to 12 hours.

The reaction in the step (42) performed in a solvent can provide a solution containing the compound (42) after completion of the reaction. Optionally, the compound (42) at high purity may be collected therefrom by adding water to the solution, leaving the mixture to stand and thereby separating the mixture into two phases, collecting the aqueous phase, and evaporating the solvent. When the compound (42) contains a group represented by —OSO$_3$H (i.e., when X is H), an alkaline aqueous solution such as a sodium hydrogen carbonate aqueous solution or ammonia water may be used instead of water to convert the —OSO$_3$H group into a sulfuric acid salt group.

The resulting compounds may be subjected to any of evaporation of a solvent or operations such as distillation and purification after the respective steps, whereby the purity of each compound may be increased.

EXAMPLES

The invention is described hereinbelow with reference to examples. Still, these examples are not intended to limit the invention.

The parameters in the examples were determined by the following methods.

Example 1

A mixture of lithium (2.0 g), dimethylphenylchlorosilane (8.4 g), and tetrahydrofuran (120 mL) was stirred at room temperature for six hours. To the reaction solution was added 4-(tert-butyldimethylsiloxy)-1-morpholinobutan-1-one (10 g), and the mixture was stirred at −78° C. for two hours. To the reaction solution, was added a saturated ammonium chloride aqueous solution (300 mL). The mixture was subjected to extraction with ethyl acetate. The extract was dried over sodium sulfate and the solvent was evaporated under reduced pressure. The residue was then purified by silica gel column chromatography. Thereby, 4-(tert-butyldimethylsiloxy) -1- (dimethyl (phenyl) silyl) butan-1-one (6.4 g) was obtained.

$^1$H-NMR (CDCl$_3$) δppm: −0.01 (s, 6H), 0.49 (s, 6H), 0.85 (s, 9H), 1.61-1.71 (m, 2H), 2.66 (J=7.0, t, 2H), 3.51 (J=6.2, t, 2H), 7.38-7.40 (m, 3H), 7.53-7.57 (m, 2H)

A mixture of 4-(tert-butyldimethylsiloxy)-1-(dimethyl (phenyl)silyl)butan-1-one (6.4 g), 1-octen-3-one (2.41 g), 3-ethyl-5-(2-hydroxyethyl)-4-methylthiazolium bromide (1.42 g), 1,8-diazabicyclo[5.4.0]-7-undecene (0.86 g), isopropanol (3.17 g), and tetrahydrofuran (11.5 mL) was stirred at 75° C. for eight hours. The solvent in the reaction solution was evaporated under reduced pressure, and the residue was then purified by silica gel column chromatography. Thereby, 1-tert-butyldimethylsiloxydodecane-4,7-dione (4.0 g) was obtained.

$^1$H-NMR (CDCl$_3$) δppm: 0.02 (s, 6H), 0.88 (s, 12H), 1.22-1.31 (m, 4H), 1.51-1.59 (m, 2H), 1.72-1.83 (m, 2H), 2.43 (J=7.6, t, 2H), 2.55 (J=7.6, t, 2H), 2.67 (s, 4H), 3.59 (J=5.9, t, 2H)

A mixture of 1-tert-butyldimethylsiloxydodecane-4,7-dione (1.9 g), a 1 M solution (15 mL) of tetrabutylammonium fluoride in tetrahydrofuran, and tetrahydrofuran (17.5 mL) was stirred at 0° C. for two hours. To the reaction solution was added a saturated ammonium chloride solution (100 mL). The mixture was subjected to extraction with ethyl acetate. The extract was dried over sodium sulfate and the solvent was evaporated under reduced pressure. The residue was then purified by silica gel column chromatography. Thereby, 1-hydroxydodecane-4,7-dione (2.0 g) was obtained.

$^1$H-NMR (CDCl$_3$) δppm: 0.89 (s, 3H), 1.24-1.33 (m, 4H), 1.52-1.58 (m, 2H), 1.81-1.90 (m, 2H), 2.45 (J=7.6, t, 2H), 2.63 (J=7.0, t, 2H), 2.76 (s, 4H), 3.65 (J=5.9, t, 2H)

A mixture of 1-hydroxydodecane-4,7-dione (1.9 g), chlorosulfonic acid (1.3 g), triethylamine (1.79 g), and diethyl ether (30 mL) was stirred at room temperature for two hours. To the reaction solution was added 10 mL of a 10% sodium hydrogen carbonate aqueous solution. The aqueous phase was washed with ethyl acetate, and the solvent was evaporated under reduced pressure. The resulting residue was dissolved in 20 mL of deionized water and 100 mL of acetone was added thereto. A precipitate was removed and the solvent in the filtrate was evaporated under reduced pressure. The residue was then extracted with methanol and the solvent in the extracted solution was evaporated under reduced pressure. Thereby, sodium 4,7-dioxododecyl sulfate (2.4 g) was obtained.

$^1$H-NMR (D$_2$O) δppm: 0.67 (J=6.8, t, 3H), 1.04-1.14 (m, 4H), 1.31-1.42 (m, 2H), 1.72-1.79 (m, 2H), 2.36 (J=7.3, t, 2H), 2.54 (J=7.3, t, 2H), 2.62 (s, 4H), 3.86 (J=6.2, t, 2H)

Sodium 4,7-dioxododecyl sulfate was dissolved in water so as to give the concentration shown in Table 1, and the surface tension was determined by the Wilhelmy method at 20° C. The results are shown in Table 1.

TABLE 1

| Amount of compound relative to water (wt %) | Surface tension (mN/m) |
| --- | --- |
| 0.001 | 67.8 |
| 0.01 | 72.1 |
| 0.1 | 50.6 |
| 1 | 31.5 |
| 5 | 24.7 |

Example 2

Divinyl ketone (7.4 g), 2-methylfuran (8.0 g), acetic acid (6 mL), and water (60 mL) were stirred at 40° C. for four hours. The reaction solution was added to a saturated sodium hydrogen carbonate solution. The mixture was subjected to extraction with ethyl acetate. The extract was dried over sodium sulfate and the solvent was evaporated under reduced pressure. The residue was then purified by silica gel column chromatography. Thereby, 1-(5-methyl-2-furanyl)-3-buten-2-one (7.4 g) was obtained.

$^1$H-NMR (CDCl$_3$) δppm: 5.88 (dd, J=17.4, 10.6, 2H), 6.32 (dd, J=17.4, 1.3, 2H), 5.88 (dd, J=10.6, 1.3, 2H)

A mixture of 1-(5-methyl-2-furanyl)-3-buten-2-one (1.7 g), 4-(tert-butyldimethylsiloxy)-1-(dimethyl(phenyl)silyl) butan-1-one (4.8 g), 3-ethyl-5-(2-hydroxyethyl)-4-methylthiazolium bromide (1.42 g), 1,8-diazabicyclo[5.4.0]-7-undecene (0.66 g), isopropanol (3.4 g), and tetrahydrofuran (11.5 mL) was stirred at 75° C. for eight hours. The solvent in the reaction solution was evaporated under reduced pressure, and the residue was then purified by silica gel column chromatography. Thereby, 8-((tert-butyldimethylsilyl)oxy)-1-(5-methylfuran-2-yl)octane-2,5-dione (1.9 g) was obtained.

A mixture of 8-((tert-butyldimethylsilyl)oxy)-1-(5-methylfuran-2-yl)octane-2,5-dione (1.9 g), a 1 M solution (7 mL) of tetrabutylammonium fluoride in tetrahydrofuran, and tetrahydrofuran (5 mL) was stirred at 0° C. for two hours. To the reaction solution was added a saturated ammonium chloride solution (100 mL). The mixture was subjected to extraction with ethyl acetate. The extract was dried over sodium sulfate and the solvent was evaporated under reduced pressure. The residue was then purified by silica gel column chromatography. Thereby, 8-hydroxy-1-(5-methylfuran-2-yl)octane-2,5-dione (1.0 g) was obtained.

A mixture of 8-hydroxy-1-(5-methylfuran-2-yl)octane-2,5-dione (1.0 g), chlorosulfonic acid (0.5 g), triethylamine (0.8 g), and diethyl ether (10 mL) was stirred at room temperature for two hours. To the reaction solution was added 10 mL of a 10% sodium hydrogen carbonate aqueous solution. The aqueous phase was washed with ethyl acetate and the solvent was evaporated under reduced pressure. The resulting residue was dissolved in 20 mL of deionized water and 100 mL of acetone was added thereto. A precipitate was removed and the solvent in the filtrate was evaporated under reduced pressure. The residue was then extracted with methanol and the solvent in the extracted solution was evaporated under reduced pressure. Thereby, sodium 9-(5-methylfuran-2-yl)-4,7-dioxononyl sulfate (0.8 g) was obtained.

A mixture of sodium 9-(5-methylfuran-2-yl)-4,7-dioxononyl sulfate (0.8 g) and 1 M hydrochloric acid (3 mL) was stirred at 100° C. for one hour. To the reaction solution was added a NaOH aqueous solution (0.2 M) so as to neutralize the reaction solution, and the mixture was then concentrated. The concentrated product was purified by reprecipitation with acetone and water. Thereby, sodium 4,7,10,13-tetraoxotetradecyl sulfate (0.75 g) was obtained.

Sodium 4,7,10,13-tetraoxotetradecyl sulfate was dissolved in water so as to give the concentration shown in Table 2, and the surface tension was determined by the Wilhelmy method at 20° C. The results are shown in Table 2.

TABLE 2

| Amount of compound relative to water (wt %) | Surface tension (mN/m) |
|---|---|
| 0.001 | 68.7 |
| 0.01 | 67.2 |
| 0.1 | 58.6 |
| 1 | 36.6 |
| 5 | 35.7 |

INDUSTRIAL APPLICABILITY

The compound of the invention can favorably reduce the surface tension of water.

The compound of the invention can suitably be used as a surfactant.

The compound of the invention can suitably be used as a surfactant promoter (in particular, a surfactant promoter for agents such as coating material, lacquer, and adhesive).

The compound of the invention can suitably be used as a viscosity reducing agent, for example.

The compound of the invention can suitably be used as a dispersant, in particular an aqueous dispersant, for example.

The compound of the invention can suitably be used as an emulsifier, for example.

The invention claimed is:

1. A compound represented by the following formula:

[Chem. 1]

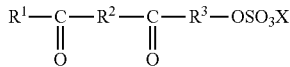

wherein
$R^1$ is a linear or branched alkyl group containing one or more carbon atoms or a cyclic alkyl group containing three or more carbon atoms, with a hydrogen atom that binds to a carbon atom being optionally replaced by a hydroxy group or a monovalent organic group containing an ester bond, the alkyl group optionally containing a carbonyl group when containing two or more carbon atoms, and the alkyl group optionally containing a monovalent or divalent heterocycle or being optionally in a cyclized form when containing three or more carbon atoms;

$R^2$ and $R^3$ are each individually a linear or branched alkylene group containing one or more carbon atoms, or a cyclic alkylene group containing three or more carbon atoms, with a hydrogen atom that binds to a carbon atom being optionally replaced by a hydroxy group or a monovalent organic group containing an ester bond;

$R^1$, $R^2$, and $R^3$ contain six or more carbon atoms in total;

X is H, a metal atom, $NR^4_4$, imidazolium optionally containing a substituent, pyridinium optionally containing a substituent, or phosphonium optionally containing a substituent, where $R^4$s are each H or an organic group and are the same as or different from each other; and any two of $R^1$, $R^2$, and $R^3$ optionally bind to each other to form a ring.

2. The compound according to claim 1, wherein in the formula, $R^1$ is a C1-C8 linear or branched alkyl group containing no carbonyl group, a C3-C8 cyclic alkyl group containing no carbonyl group, a C2-C45 linear or branched alkyl group containing 1 to 10 carbonyl groups, a C3-C45 cyclic alkyl group containing a carbonyl group, or a C3-C45 alkyl group containing a monovalent or divalent heterocycle.

3. The compound according to claim 1, wherein in the formula, $R^1$ is a group represented by the following formula:

[Chem. 2]

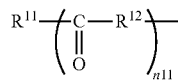

wherein n11 is an integer of 0 to 10; $R^{11}$ is a C1-C5 linear or branched alkyl group or a C3-C5 cyclic alkyl group; and $R^{12}$ is a C0-C3 alkylene group, and when n11 is an integer of 2 to 10, $R^{12}$s are the same as or different from each other.

4. The compound according to claim 1, wherein in the formula, $R^2$ and $R^3$ are each individually a linear or branched alkylene group containing no carbonyl group and containing one or more carbon atoms.

5. The compound according to claim 1, wherein in the formula, $R^2$ and $R^3$ are each individually a C1-C3 linear or branched alkylene group containing no carbonyl group.

6. A surfactant comprising the compound according to claim 1.

7. An aqueous dispersant comprising the compound according to claim 1.

* * * * *